United States Patent
Iwasaki

(10) Patent No.: US 12,408,820 B2
(45) Date of Patent: Sep. 9, 2025

(54) ENDOSCOPE AND ENDOSCOPE SYSTEM

(71) Applicant: OLYMPUS MEDICAL SYSTEMS CORP., Tokyo (JP)

(72) Inventor: Seiji Iwasaki, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 269 days.

(21) Appl. No.: 18/122,197

(22) Filed: Mar. 16, 2023

(65) Prior Publication Data

US 2023/0292993 A1    Sep. 21, 2023

Related U.S. Application Data

(60) Provisional application No. 63/320,772, filed on Mar. 17, 2022.

(51) Int. Cl.
*A61B 1/00* (2006.01)
*A61B 1/015* (2006.01)

(52) U.S. Cl.
CPC ...... *A61B 1/00094* (2013.01); *A61B 1/00039* (2013.01); *A61B 1/015* (2013.01)

(58) Field of Classification Search
CPC . A61B 1/00094; A61B 1/00039; A61B 1/015; A61B 1/00135; A61B 1/00089; A61B 1/00137
See application file for complete search history.

(56) References Cited

FOREIGN PATENT DOCUMENTS

| JP | 368325 Z | 12/1949 |
|----|----------|---------|
| JP | H10-179510 A | 7/1998 |

*Primary Examiner* — Timothy J Neal
(74) *Attorney, Agent, or Firm* — Morgan, Lewis & Bockius LLP

(57) ABSTRACT

An endoscope comprising an insertion section including a distal end portion, a distal end opening in a distal end surface of a distal end portion, a side opening in a side surface of the distal end portion, a suction channel located in the insertion section and extending proximally from the distal end portion, and a valve switchable between an open state and a closed state. When a first suctioning flow through the distal end opening is less than a minimum suctioning flow, the valve is in the open state and a second suctioning flow through the side opening is present, and when the first suctioning flow is more than the minimum suctioning flow, the valve is in the closed state and the second suctioning flow is absent.

20 Claims, 8 Drawing Sheets

ENDOSCOPE AND ENDOSCOPE SYSTEM

RELATED APPLICATION DATA

This application is based on and claims priority under 35 U.S.C. § 119 to U.S. Provisional Application No. 63/320,772 filed on Mar. 17, 2022, the entire contents of which are incorporated herein by reference.

FIELD OF THE DISCLOSURE

The present disclosure relates to an endoscope including a suction function, and an endoscope unit.

BACKGROUND

In examination and treatment using an endoscope, blood and the like have to be suctioned to identify a bleeding part at a time when there is bleeding inside a subject. For example, Japanese Patent Application Laid-Open Publication No. H10-179510 discloses a technique with which suction inside a body cavity or the like may be efficiently performed in a case where a distal end of a passage for suction provided in a distal end rigid portion is opened from a distal end surface of an insulating cap along a side surface and is used as a suction passage.

SUMMARY OF THE DISCLOSURE

An endoscope according to an aspect of the present disclosure includes: an insertion section including a distal end portion; a distal end opening in a distal end surface of the distal end portion; a side opening in a side surface of the distal end portion; a suction channel located in the insertion section and extending proximally from the distal end portion, wherein the suction channel is in communication with the distal end opening and with the side opening; and a valve switchable between an open state and a closed state, wherein when a first suctioning flow through the distal end opening is less than a minimum suctioning flow, the valve is in the open state and a second suctioning flow through the side opening is present, and wherein, when the first suctioning flow through the distal end opening is more than the minimum suctioning flow, the valve is in the closed state and the second suctioning flow through the side opening is absent.

An endoscope system according to an aspect of the present disclosure includes: an endoscope, wherein the endoscope includes: an insertion section including a distal end portion, a first opening in a distal end surface of the distal end portion, a second opening in a side surface of the distal end portion; and a suction channel located in the insertion section and extending proximally from the distal end portion, wherein the suction channel is in communication with the distal end opening and with the side opening, a distal cover attached to the distal end portion, wherein the distal cover includes: a valve switchable between open state and closed state, wherein, when a first suctioning flow through the distal end opening is less than a minimum suctioning flow, the valve is in the open state and a second suctioning air flow through the side opening is present, and wherein, when the first suctioning flow through the distal end opening is more than the minimum suctioning flow, the valve is in the closed state and the second suctioning flow through the side opening is absent.

DETAILED DESCRIPTION

Hereinafter, a configuration of an aspect of the present disclosure will be described. Note that in the following description, the drawings based on the embodiment are schematic, and a relationship between a thickness and a width of each part, a ratio of respective thicknesses of parts, and the like are different from actual relationships. Moreover, dimensional relationships, ratios and the like may be different between drawings.

At a time of performing suction inside a subject using an endoscope, a body cavity wall or the like may stick to a distal end portion of an insertion section to completely block a channel opening or to reduce an opening amount. Particularly, when the body cavity wall or the like sticks to the channel opening at a time of performing suction of blood or the like by the endoscope to treat bleeding, suction of blood or the like cannot be continued.

In such a case, a suction operation by the endoscope has to be suspended, the distal end portion of the insertion section has to be separated from the body cavity wall or the like, and the suction operation has to be resumed, thus making treatment burdensome and time-consuming.

Accordingly, the present disclosure is aimed at providing an endoscope and an endoscope system with which suction may be continued without being interrupted even when a channel opening is blocked by a body cavity wall or the like or an opening amount is reduced, and with which time and burden of treatment may be reduced.

Figure 1:
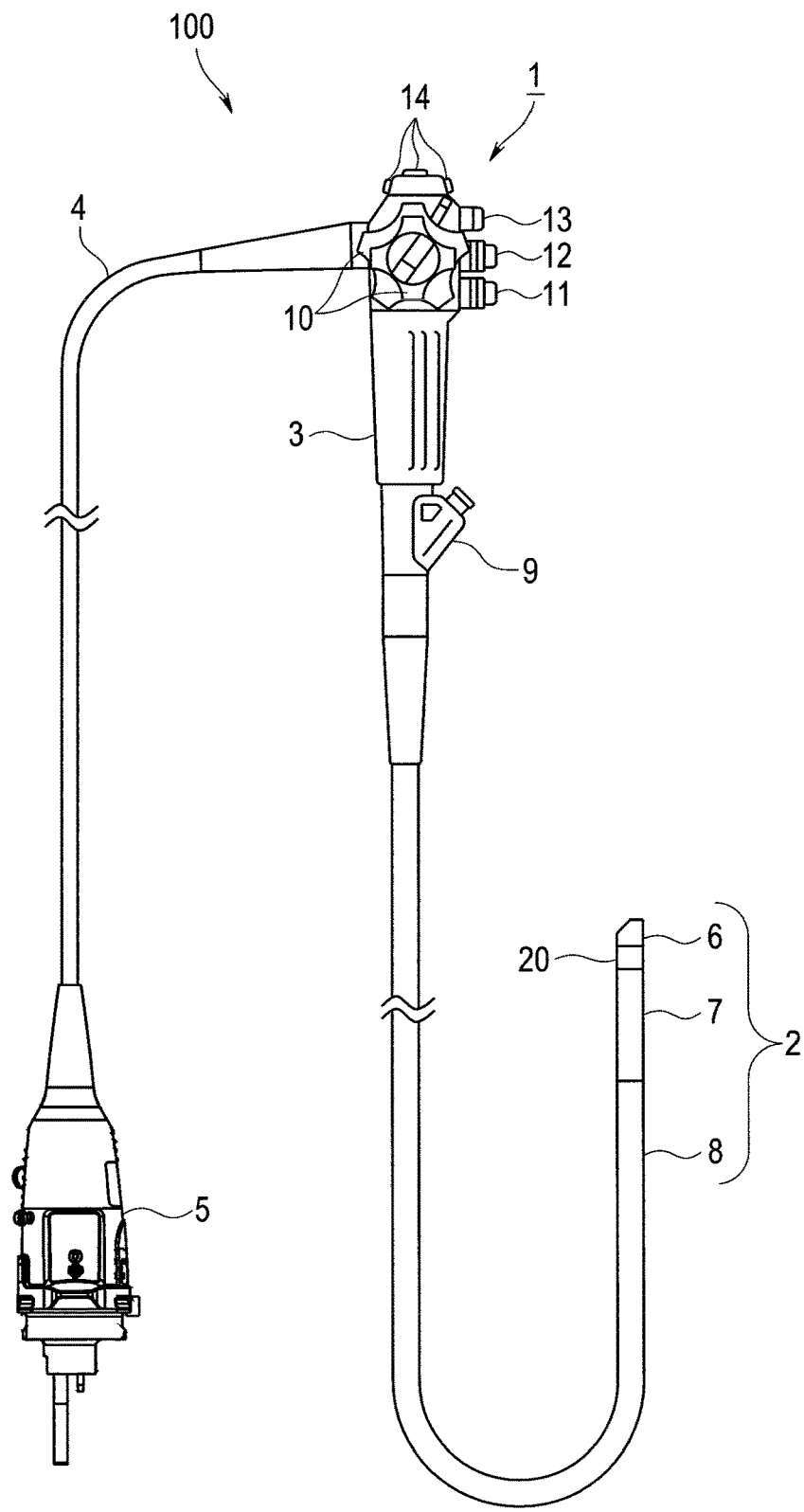
FIG. 1 is a diagram schematically showing an endoscope system of an aspect of the present disclosure.

In the following, a description will be given of an endoscope system 100 of a present embodiment. As shown in FIG. 1, the endoscope system 100 includes an endoscope 1, and a cover member 20 that is a distal end opening/closing cover. Note that a configuration is also possible where the cover member 20 is included in the endoscope 1.

The endoscope 1 includes an insertion section 2, an operation section 3, a universal cord 4, and an endoscope connector 5. The insertion section 2 is a long member that can be inserted inside a subject. The insertion section 2 includes a distal end portion 6, a bending portion 7, and a flexible tube portion 8.

The distal end portion 6 is disposed on a distal end of the insertion section 2. The bending portion 7 is disposed on a proximal end side of the distal end portion 6. The bending portion 7 is an active bending part and is freely bendable. The flexible tube portion 8 has flexibility, and is disposed on a proximal end side of the bending portion 7. The flexible tube portion 8 is a passive flexible part, and is connected on a distal end side of the operation section 3.

A pair of angle knobs 10 for performing bending of the bending portion 7 are provided on the operation section 3. An air/water feeding button 11, a suction button 12, and a plurality of video-related switches 13, 14 configured to perform operations related to freezing of an endoscope image, releasing of image pickup, and the like are provided on the operation section 3.

The universal cord 4 is a composite cable extending from a side portion of the operation section 3. The endoscope connector 5 is provided on an extension end of the universal cord 4. The endoscope connector 5 is connected to a video processor, not shown, of a camera control unit (CCU) including a light source device.

Moreover, the suction button 12 enables, by being pressed down, suction of foreign substances such as excrement, undigested substances and blood inside a subject by a suction device that is not shown. Note that a treatment instrument insertion channel, described later, is provided from the insertion section 2 to the operation section 3, and the foreign substances are suctioned through the treatment instrument insertion channel.

The endoscope 1 configured in the above manner is desirably a disposable single-use endoscope that is disposed of after use (after being used once), but may of course be a reusable product that is re-used after being subjected to a disinfecting/sterilizing process.

Figure 2:
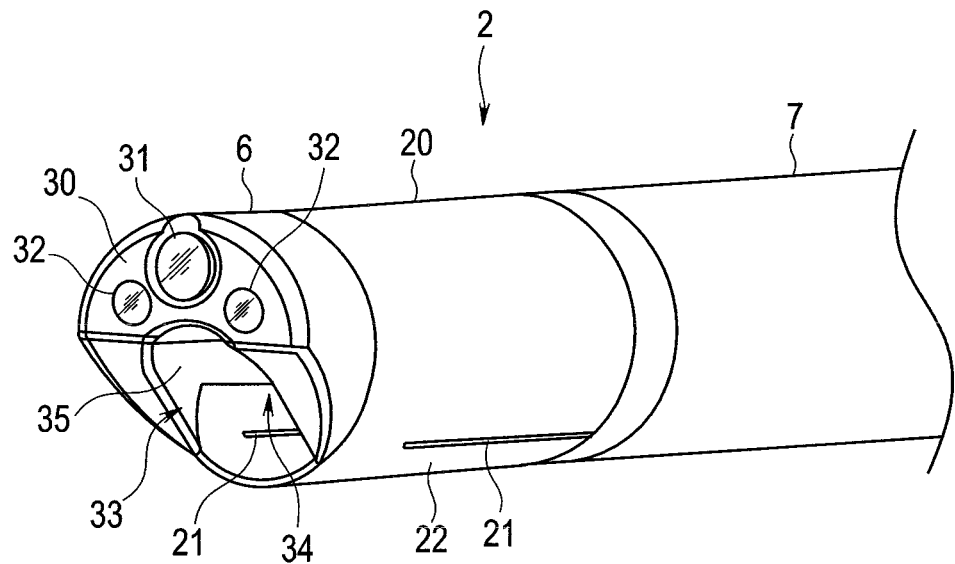
FIG. 2 is a perspective view showing a configuration of a distal end part of an insertion section to which a cover member is attached.
Figure 3:
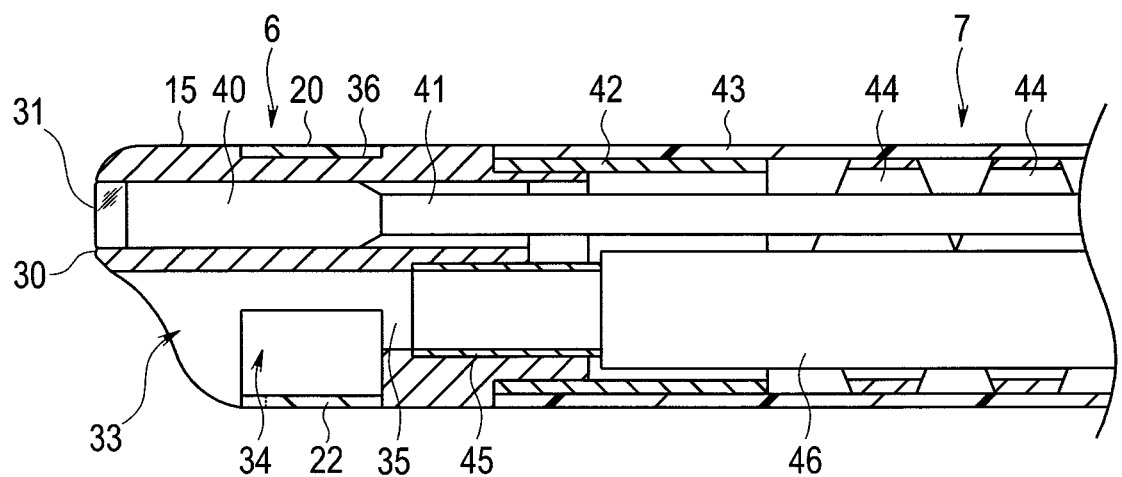
FIG. 3 is a cross-sectional view showing the configuration of the distal end part of the insertion section to which the cover member is attached.

As shown in FIGS. 2 and 3, the distal end portion 6 of the insertion section 2 includes a distal end structural member 15 that is made of metal or the like and that is formed into a bullet shape. An observation window 31 and an illumination window 32 are provided in a distal end surface 30 of the distal end structural member 15.

Photographing light entering from the observation window 31 is photoelectrically converted by an image pickup unit 40 built inside the distal end portion 6. An image pickup cable 41 extending from the image pickup unit 40 is inserted through the insertion section 2, the operation section 3, and the universal cord 4, up to the endoscope connector 5.

Illumination light is radiated toward the subject from the illumination window 32. The illumination light is transmitted by a light guide that is not shown. The light guide is inserted through the insertion section 2, the operation section 3, and the universal cord 4, up to the endoscope connector 5. Note that the illumination light is emitted by a light source that is built inside the video processor.

The endoscope 1 here is configured such that the illumination light emitted from the video processor is transmitted by the light guide, but instead, a light source such as an LED may be provided in the distal end portion 6.

As shown in FIG. 3, a bending rubber connection tube 42 is fitted on a proximal end of the distal end structural member 15. The bending rubber connection tube 42 is connected while being covered by a distal end part of a bending rubber 43. Note that the bending rubber 43 covers a plurality of bending pieces 44 provided on the bending portion 7 in an integrated manner.

A channel conduit 35 is provided in the distal end structural member 15. A distal end opening portion 33 of the channel conduit 35 is formed in the distal end surface 30 of the distal end structural member 15. In other words, the distal end opening portion 33 is an opening on a front side of the channel conduit 35.

A channel connection tube 45 that communicates with the channel conduit 35 is fitted in the distal end structural member 15. A distal end part of a treatment instrument insertion channel 46 that functions also as a suction channel is connected to the channel connection tube 45.

A side surface opening portion 34 is formed in a side surface of the distal end structural member 15, the side surface opening portion 34 being formed by being cut out up to the channel conduit 35. In other words, the side surface opening portion 34 is a lateral opening of the channel conduit 35. The side surface opening portion 34 communicates with the treatment instrument insertion channel 46. Accordingly, the distal end structural member 15 is provided with the side surface opening portion 34 that is on a lateral side and that communicates with the distal end opening portion 33 on a front side.

A groove 36 is formed on the distal end structural member 15, the groove 36 being formed around a longitudinal axis on an outer circumferential portion along the side surface opening portion 34. The groove 36 is a bottomed groove portion that is formed in a recessed manner in a circumferential direction at a position of the side surface opening portion 34 of the distal end structural member 15.

Figure 4:
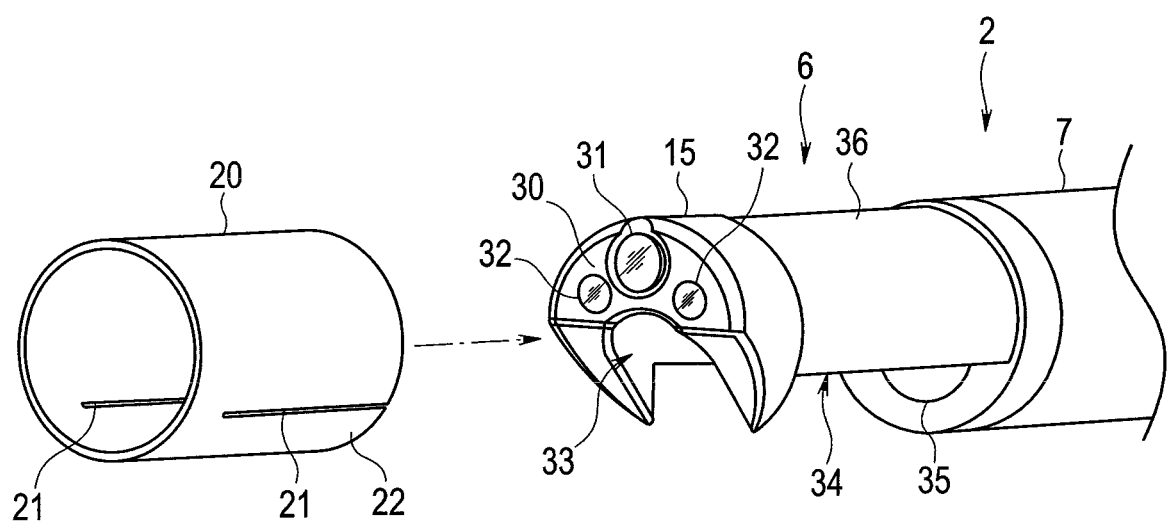
FIG. 4 is an exploded perspective view showing the cover member, and the distal end part of the insertion section before the cover member is attached.

The cover member 20 is attached to the groove 36. Note that as shown in FIG. 4, the cover member 20 is engaged by being fitted to cover the groove 36 from a distal end side of the distal end structural member 15. The cover member 20 is a disposable single-use cover member that is disposed of after use (after being used once).

Figure 5:
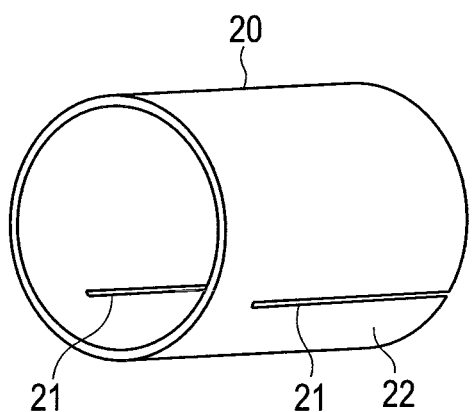
FIG. 5 is a perspective view showing a configuration of the cover member.
Figure 6:
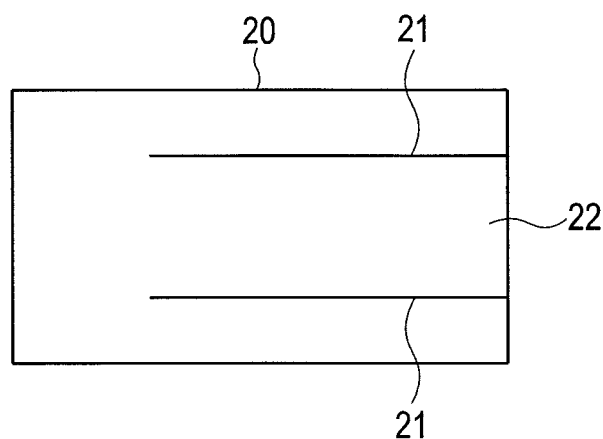
FIG. 6 is a plan view showing the configuration of the cover member where an open/close valve is formed by two slits.

As shown in FIGS. 5 and 6, the cover member 20 is a cylindrical body that is formed from an elastic material such as elastomer or silicone rubber. The cover member 20 includes two slits 21 that are straight and that are formed from positions close to a distal end side to a proximal end.

The two slits 21 are formed to be parallel to each other with a predetermined distance in between in a circumferential direction of the cover member 20. A gap between the two slits 21 is set smaller than a width range (region) of the side surface opening portion 34 orthogonal to a longitudinal axis of the distal end structural member 15.

An open/close valve 22 (secondary body) is formed between the two slits 21, the open/close valve 22 being an opening/closing portion that is arch-shaped in a cross-sectional direction and rectangular in a planar direction. Normally, the open/close valve 22 is retained by an elastic force such that the cover member 20 is maintained in a substantially cylindrical shape.

Note that the open/close valve 22 is arch-shaped in the cross-sectional direction, and is not easily deformed to open outward relative to the distal end portion 6. Accordingly, unintended deformation of the open/close valve 22 in an outward direction relative to the distal end portion 6 may be prevented.

The cover member 20 is attached by being engaged with the groove 36 of the distal end structural member 15. The side surface opening portion 34 is thus covered by the cover member 20.

Note that a depth of the groove 36 and a thickness of the cover member 20 are substantially the same. A length of the groove 36 and a length of the cover member 20 in a longitudinal axis direction are also substantially the same. Accordingly, the cover member 20 is attached in such a way that an outer circumferential surface of the cover member 20 is on a substantially same plane with an outer surface of the distal end structural member 15 with no step between the two.

Note that the cover member 20 is attached to the groove 36 of the distal end structural member 15 in such a way that, in relation to positions around an axis, the two slits are positioned within the width range of the side surface opening portion 34. Accordingly, the open/close valve 22 formed by the two slits 21 is positioned within the width range of the side surface opening portion 34.

With the endoscope system 100 configured in the above manner, normally, the open/close valve 22 of the cover member 20 attached to the distal end portion 6 is in a closed state, as shown in FIGS. 2 and 3. In other words, the cover member 20 is substantially cylindrically shaped, with the open/close valve retained by the elastic force.

Accordingly, the side surface opening portion 34 formed in the distal end structural member 15 of the distal end portion 6 is closed by being entirely covered by the cover member 20. Accordingly, the channel conduit 35 of the distal end structural member 15 is open only at the distal end opening portion 33.

When suction is performed in the state described above, the endoscope system 100 suctions foreign substances such as excrement, undigested substances and blood inside the subject from the distal end opening portion 33. Suction is performed from the distal end opening portion 33, through the channel conduit 35 and the treatment instrument insertion channel 46.

Note that because the open/close valve 22 is closed, air and the like inside the body cavity are not suctioned through the side surface opening portion 34 on an outer circumferential side of the distal end portion 6 of the endoscope 1, and reduction in a suction force may be prevented.

Figure 7:
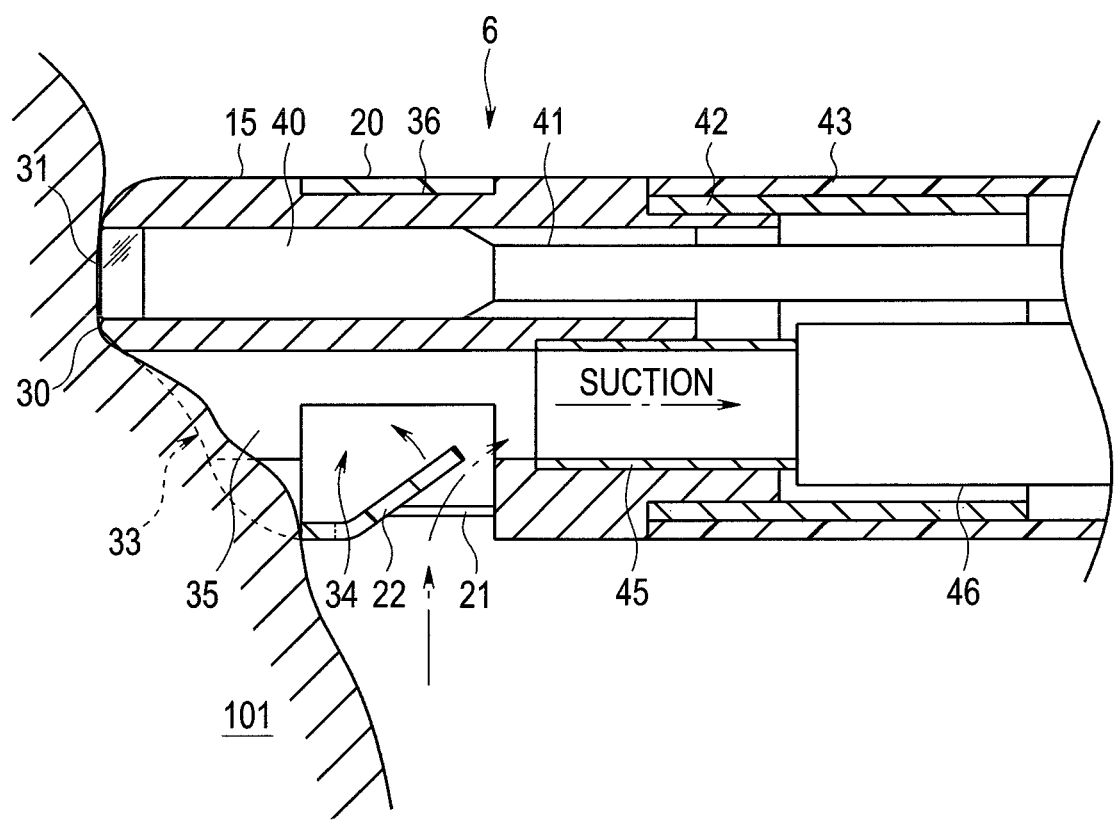
FIG. 7 is a cross-sectional view showing a state where a distal end portion is in contact with a body cavity wall and a distal end opening portion is blocked.

As shown in FIG. 7, the endoscope system 100 may perform suction while the distal end surface 30 of the distal end portion 6 of the insertion section 2 is in contact with a body cavity wall 101. The body cavity wall 101 such as a stomach wall sticks to the distal end opening portion 33 due to the suction force. At this time, the distal end opening portion 33 is placed in a completely blocked state or in a state where an opening amount is reduced due to the body cavity wall 101.

In this state, negative pressure with predetermined magnitude is generated inside the channel conduit 35 of the distal end structural member 15 from the treatment instrument insertion channel 46. Due to the negative pressure, the open/close valve 22 of the cover member 20 moves in such a way as to be drawn into the channel conduit 35. In other words, the open/close valve 22 deforms toward an inside of the channel conduit 35, and the side surface opening portion 34 is placed in an open state. The channel conduit 35 of the distal end structural member 15 is thus opened at the side surface opening portion 34.

In this state, the endoscope system 100 is able to suction foreign substances such as excrement, undigested substances and blood inside the subject from the side surface opening portion 34. The suction is performed from the side surface opening portion 34, through the channel conduit 35 and the treatment instrument insertion channel 46.

As described above, the endoscope system 100 may continue performing suction without being interrupted even when the distal end opening portion 33 of the distal end portion 6 of the insertion section 2 adheres to the body cavity wall 101 such as a stomach wall or the opening amount is reduced during suction. This is because the open/close valve 22 of the cover member 20 covering the side surface opening portion 34 is opened due to the negative pressure generated inside the channel conduit 35 from the treatment instrument insertion channel 46.

Note that when the distal end opening portion 33 is blocked by the body cavity wall 101, the open/close valve 22 moves by being deformed by the suction force of the endoscope 1 and the side surface opening portion 34 is thus opened. Settings here are appropriately managed based on a length, a shape, a material, a thickness and the like of the two slits 21 formed in the cover member 20.

According to the description given above, at the time of suction inside a subject by the endoscope 1, the endoscope system 100 may continue performing suction through the side surface opening portion 34 without being interrupted even when the body cavity wall 101 such as a stomach wall sticks to the distal end portion 6 of the insertion section 2 and the distal end opening portion 33 of the channel opening is blocked or the opening amount is reduced. Accordingly, a suction procedure may be performed with high responsiveness.

Accordingly, with the endoscope system 100, time and burden of a task of suspending suction by the endoscope 1, separating the distal end portion 6 of the insertion section 2 from the body cavity wall 101, and resuming suction may be eliminated. Accordingly, with the endoscope system 100, a suction treatment may be performed more efficiently than with a conventional configuration.

Note that, depending on the length, the shape, the material, the thickness and the like of the two slits 21 formed in the cover member 20, an amount of deformation of the open/close valve 22 is set in the following manner, for example. Here, an opening amount of the side surface opening portion 34 that is moved due to deformation of the open/close valve 22 at a time when the distal end opening portion 33 is completely blocked by the body cavity wall 101 (100%) is taken as a reference value (100%).

In a case where the distal end opening portion 33 is blocked 70% by the body cavity wall 101 and the opening amount is 30%, the open/close valve 22 is deformed such that the opening amount of the side surface opening portion 34 is 10% relative to the reference value. The minimum suctioning flow causing deformation of the open/close valve 22 is 30% about the opening amount of the distal end opening portion 33.

Furthermore, in a case where the distal end opening portion 33 is blocked 80% by the body cavity wall 101 and the opening amount is 20%, the open/close valve 22 is deformed such that the opening amount of the side surface opening portion 34 is 30% relative to the reference value.

Moreover, in a case where the distal end opening portion 33 is blocked 90% by the body cavity wall 101 and the opening amount is 10%, the open/close valve 22 is deformed such that the opening amount of the side surface opening portion 34 is 50% relative to the reference value.

The suctioning flow can include air and liquid, such as blood. Also, the cases described above are merely examples, and various amounts of deformation may be set for the open/close valve 22 depending on the length, the shape, the material, the thickness and the like of the two slits 21 formed in the cover member 20.

(Modification)
(First Modification)

Figure 8:
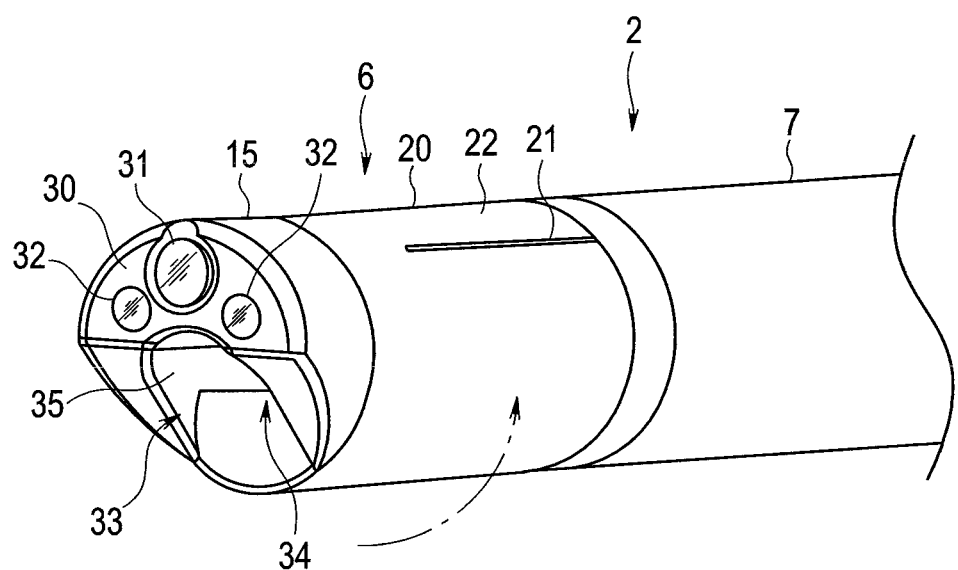
FIG. 8 is a perspective view showing a configuration of the distal end part of the insertion section to which the cover member of a first modification is attached.

In the case where suction from a side surface of the distal end portion 6 is not necessary, the endoscope system 100 may cause the open/close valve 22 to be moved outside the region of the side surface opening portion 34, as shown in FIG. 8. More specifically, the cover member 20 may be used by being rotated around the axis. In this case, the endoscope 1 performs suction of foreign substances only through the distal end opening portion 33.

(Second Modification)

Figure 9:
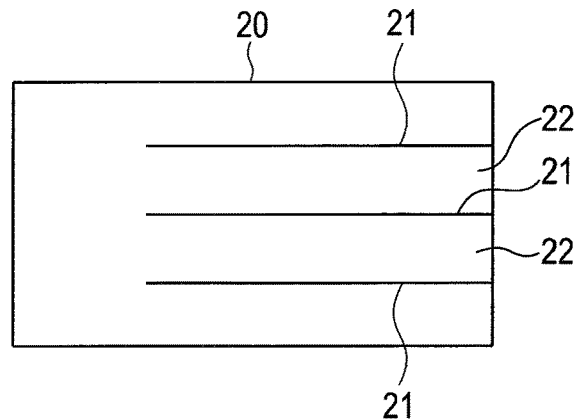
FIG. 9 is a plan view according to a second modification, showing the configuration of the cover member where three slits are formed.

As shown in FIG. 9, two open/close valves 22 may be formed by providing three slits 21 in the cover member 20.

When the open/close valve 22 is divided into two and a width is reduced, the two open/close valves 22 of the cover member 20 may be easily deformed. Accordingly, the two open/close valves 22 are opened even with small negative pressure that is generated inside the distal end structural member 15 due to a small suction force.

Accordingly, with the endoscope system 100, foreign substances may be easily suctioned through the side surface opening portion 34 of the distal end portion 6 when the distal end opening portion 33 is blocked by the body cavity wall 101 and the opening amount is reduced. Accordingly, the endoscope system 100 achieves better responsiveness in relation to suction from the side surface opening portion 34 in a state where the distal end opening portion 33 is blocked.

Moreover, in a state where one of the two open/close valves 22 is in contact with the body cavity wall 101, the other open/close valve 22 is opened/closed. In other words, even when the distal end opening portion 33 and one of the open/close valves 22 blocking the side surface opening portion 34 adhere to the body cavity wall 101 of a living body, the other open/close valve 22 is deformed to open the side surface opening portion 34. Accordingly, with the endoscope system 100, suction by the endoscope 1 may be more smoothly performed. As described above, the two open/close valves 22 may be separately opened/closed depending on the situation.

(Third Modification)

Figure 10:
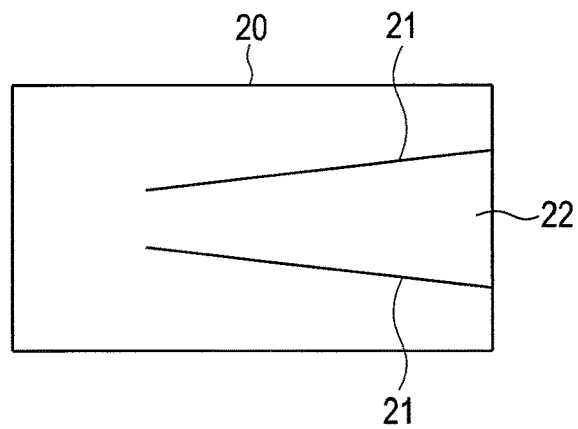
FIG. 10 is a plan view according to a third modification, showing the configuration of the cover member where the open/close valve having a small width on a distal end side is formed by two slits.

As shown in FIG. 10, the two slits 21 of the cover member 20 may be obliquely formed such that a gap of the two slits 21 is reduced toward a distal end side. In other words, the open/close valve 22 having a trapezoidal shape where the distal end side is a top side and a proximal end side is a bottom side may be formed. In other words, the two slits 21 are formed to be not parallel to each other along a longitudinal axis of the cover member 20.

Accordingly, because a width on the distal end side is small, the open/close valve 22 is easily deformed. Accordingly, the endoscope system 100 achieves better responsiveness in relation to suction from the side surface opening portion 34 in a state where the distal end opening portion 33 is blocked.

(Fourth Modification)

Figure 11:
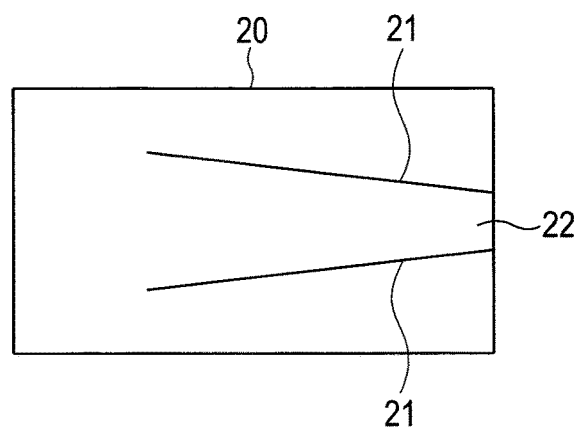
FIG. 11 is a plan view according to a fourth modification, showing the configuration of the cover member where the open/close valve having a great width on the distal end side is formed by two slits.

As shown in FIG. 11, the two slits 21 of the cover member 20 may be obliquely formed such that the gap the two slits 21 is reduced toward the proximal end side. In other words, the open/close valve 22 having a trapezoidal shape where the distal end side is the bottom side and the proximal end side is the top side may be formed. In other words, the two slits 21 are formed to be not parallel to each other along the longitudinal axis of the cover member 20.

Accordingly, because the width on the distal end side is great, the open/close valve 22 is not easily deformed on the distal end side but is easily deformed on the proximal end side. Accordingly, the negative pressure inside the distal end portion 6 of the endoscope 1 changes depending on an amount of reduction in the opening amount of the blocked distal end opening portion 33. Therefore, the width of the open/close valve 22 is increased toward a distal end, and a position at which the open/close valve 22 deforms changes according to a change in the negative pressure.

With the endoscope system 100, when the open/close valve 22 is not easily deformed on the distal end side but is easily deformed on the proximal end side, the opening amount of the side surface opening portion 34 by the open/close valve 22 may be easily controlled according to magnitude of the negative pressure inside the distal end portion 6. As a result, the open/close valve 22 of the present modification is suitable in a case where the suction force of the side surface opening portion 34 is desired to be controlled.

(Fifth Modification)

Figure 12:
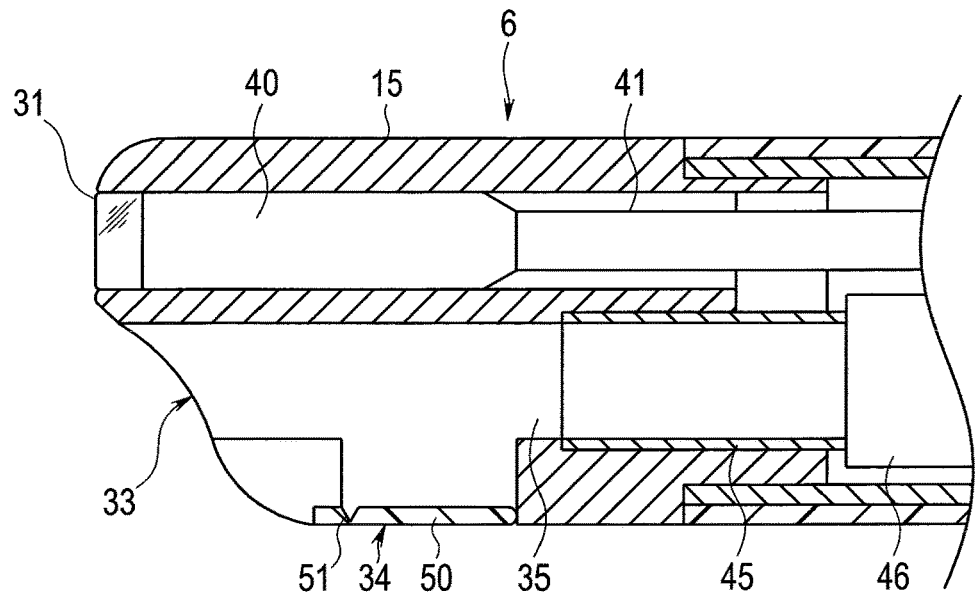
FIG. 12 is a cross-sectional view according to a fifth modification, showing the configuration of the distal end part of the insertion section where an open/close valve is provided at a distal end structural part.

As shown in FIG. 12, an open/close valve 50 having a thin plate shape may be provided at the distal end structural member 15 constituting the distal end portion 6 of the endoscope 1, without providing the cover member 20.

The open/close valve 50 is made of synthetic resin, and a groove or a thin-filmed V-shaped groove 51 is formed in a width direction on an inner surface on the distal end side. The open/close valve 50 is disposed to block the side surface opening portion 34 of the distal end structural member 15.

Figure 13:
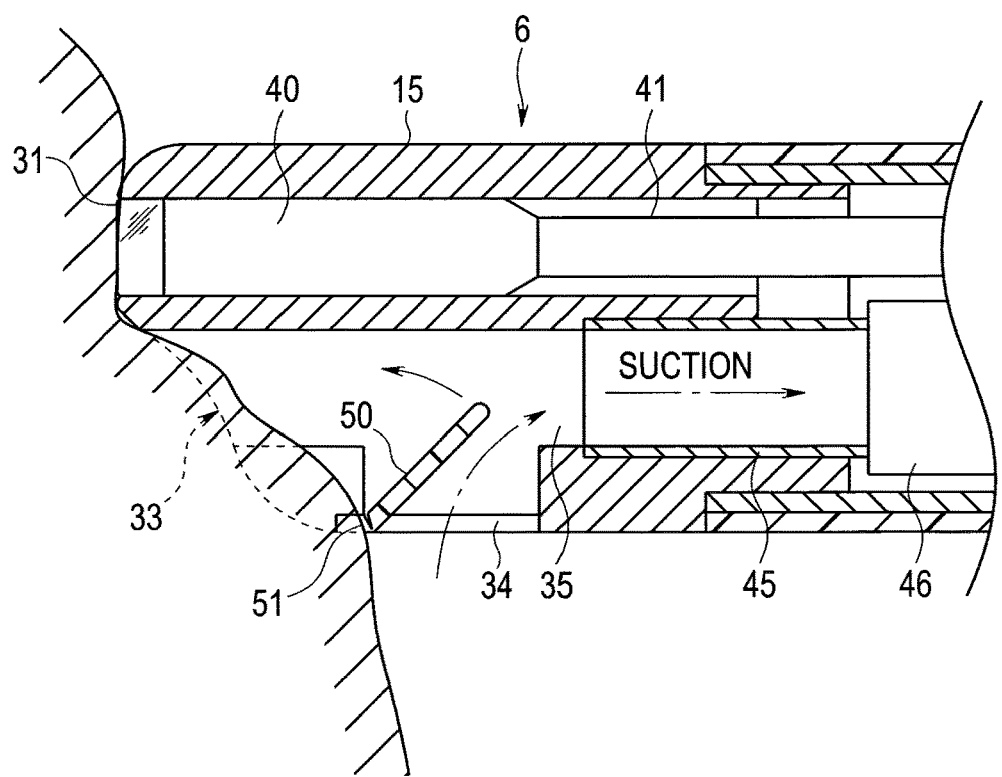
FIG. 13 is a cross-sectional view according to the fifth modification, showing a state where the distal end portion is in contact with a body cavity wall and the distal end opening portion is blocked.

As shown in FIG. 13, when the distal end opening portion 33 is blocked by the body cavity wall 101 at the time of suction and the opening amount is reduced, the open/close valve 50 moves by being deformed toward an inside of the channel conduit 35 around the V-shaped groove 51. In other words, the open/close valve 50 moves in such a way as to be drawn into the channel conduit 35 by the negative pressure with predetermined magnitude that is generated inside the channel conduit 35 of the distal end structural member 15 from the treatment instrument insertion channel 46.

The side surface opening portion 34 is thereby placed in an open state. In this state, the endoscope 1 is able to suction foreign substances such as excrement, undigested substances and blood inside the subject from the side surface opening portion 34, through the channel conduit 35 and the treatment instrument insertion channel 46.

The present disclosure is not limited to the embodiment described above, and changes may be made as appropriate within the gist or the idea of the disclosure that can be read from the claims, the entire specification, and the drawings.

What is claimed is:

1. An endoscope, comprising:
   an insertion section including a distal end portion;
   a distal end opening in a distal end surface of the distal end portion;
   a side opening in a side surface of the distal end portion;
   a suction channel located in the insertion section and extending proximally from the distal end portion, wherein the suction channel is in communication with the distal end opening and with the side opening; and
   a valve switchable between an open state and a closed state,
   wherein, when a first suctioning flow through the distal end opening is less than a minimum suctioning flow, the valve is in the open state and a second suctioning flow through the side opening is present, and wherein, when the first suctioning flow through the distal end opening is more than the minimum suctioning flow, the valve is in the closed state and the second suctioning flow through the side opening is absent.

2. The endoscope according to claim 1, wherein the first suctioning flow is a first suctioning liquid flow and the second suctioning flow is a second suctioning liquid flow.

3. The endoscope according to claim 1, wherein the minimum suctioning flow is 30% of a reference suctioning flow, and wherein the reference suctioning flow is a suctioning flow through the distal end opening in a fully open state.

4. The endoscope according to claim 3, wherein, in the open state, the first suctioning flow and the second suctioning flow is less than the reference suctioning flow.

5. The endoscope according to claim 1, wherein the valve is switchable from the closed state to the open state by a negative pressure generated inside the suction channel.

6. The endoscope according to claim 1, further comprising a distal cover located in the distal end portion,
wherein a surface of the distal cover covers the side opening,
wherein the valve is located in the surface of the distal cover,
wherein the distal cover is rotatable relative to the distal end portion around a longitudinal axis of the distal end portion, between a first position and a second position,
wherein, in the first position, the valve is aligned with the side opening, and
wherein, in the second position, the valve is unaligned with the side opening.

7. The endoscope according to claim 6, wherein the valve includes a main body and a secondary body, and wherein the secondary body moves toward an interior space of the distal end portion by a negative pressure.

8. The endoscope according to claim 6, wherein the valve is formed by a plurality of slits provided in the distal cover.

9. The endoscope according to claim 8, wherein the plurality of slits are formed along the longitudinal axis.

10. The endoscope according to claim 8, wherein two adjacent slits of the plurality of slits are separated along the surface of the distal cover by a gap, and wherein a distance of the gap at a distal end of the slits is less than a distance of the gap at a proximal end of the slits.

11. The endoscope according to claim 8, wherein two adjacent slits of the plurality of slits are separated along the surface of the distal cover by a gap, and wherein a distance of the gap at a distal end of the slits is more than a distance of the gap at a proximal end of the slits.

12. The endoscope according to claim 1, wherein the valve is formed from an elastic material.

13. The endoscope according to claim 1, wherein the distal end surface of the distal end portion includes a first distal end surface section that is non-perpendicular to a longitudinal axis of the distal end portion, and
wherein at least a majority portion of the distal end opening is in the first distal end surface section.

14. The endoscope according to claim 13, wherein the distal end surface of the distal end portion includes a second distal end surface section that is perpendicular to a longitudinal axis of the distal end portion, and
wherein at least one of an observation window and an illumination window are located in the second distal end surface section.

15. An endoscope system, comprising:
an endoscope, wherein the endoscope includes:
an insertion section including a distal end portion,
a first opening in a distal end surface of the distal end portion,
a second opening in a side surface of the distal end portion, and
a suction channel located in the insertion section and extending proximally from the distal end portion, wherein the suction channel is in communication with the distal end opening and with the side opening; and
a distal cover attached to the distal end portion, wherein the distal cover includes:
a valve switchable between open state and closed state,
wherein, when a first suctioning flow through the distal end opening is less than a minimum suctioning flow, the valve is in the open state and a second suctioning flow through the side opening is present, and
wherein, when the first suctioning flow through the distal end opening is more than the minimum suctioning flow, the valve is in the closed state and the second suctioning flow through the side opening is absent.

16. The endoscope according to claim 15, wherein the first suctioning flow is a first suctioning liquid flow and the second suctioning flow is a second suctioning liquid flow.

17. The endoscope system according to claim 15, wherein the minimum suctioning flow is 30% of a reference suctioning flow, and wherein the reference suctioning flow is a suctioning flow through the distal end opening in a fully open state.

18. The endoscope system according to claim 17, wherein, in the open state, the first suctioning flow and the second suctioning flow is less than the reference suctioning flow.

19. The endoscope system according to claim 15, wherein the valve is switchable from the closed state to the open state by a negative pressure generated inside the suction channel.

20. The endoscope system according to claim 15, wherein the valve is formed by a plurality of slits provided in the distal cover.

* * * * *